United States Patent [19]

Simoncini

[11] 3,968,789

[45] July 13, 1976

[54] APPARATUS FOR MASSAGING THE SKIN
[76] Inventor: Giancarlo Simoncini, 47, Via Jussi, San Lazzaro di Savena, Italy, 40068
[22] Filed: Oct. 29, 1974
[21] Appl. No.: 518,589

[30] Foreign Application Priority Data
Oct. 31, 1973 Italy .................................. 12908/73

[52] U.S. Cl. .................................. 128/49; 128/65; 15/29
[51] Int. Cl.² ...................... A61H 7/00; A61H 15/00
[58] Field of Search .............. 128/48, 49, 65, 62 A, 128/41; 15/29; 401/153, 28; 222/209

[56] References Cited
UNITED STATES PATENTS

| 718,054 | 1/1903 | Head | 128/65 |
|---|---|---|---|
| 1,974,031 | 9/1934 | Merrill | 128/65 |
| 2,261,385 | 11/1941 | Kaminsky | 128/65 |
| 2,854,969 | 10/1958 | Nolan | 128/65 |
| 3,266,532 | 8/1966 | Stewart | 222/209 X |

Primary Examiner—Lawrence W. Trapp
Attorney, Agent, or Firm—Murray Schaffer

[57] ABSTRACT

A massaging apparatus comprises a casing provided with a handle, inside which casing there is housed a small electric motor capable of imparting to its shaft a movement consisting of rotary oscillations. Onto one end of the shaft of the motor there is removably mounted a circular brush. Onto the casing of the apparatus, preferably in proximity of the handle, there is arranged a small container for lotions or other suitable liquid to be spread onto the zone of the skin undergoing the massage treatment. The liquid is conveyed from the container to a dispensing bore provided in the massaging brush through a suitable canalization, consisting of a flexible pipe. The container is bellows-shaped and made of flexible material, so that, by exerting pressure onto it, a controlled amount of liquid is conveyed to the dispensing bore in the brush.

6 Claims, 6 Drawing Figures

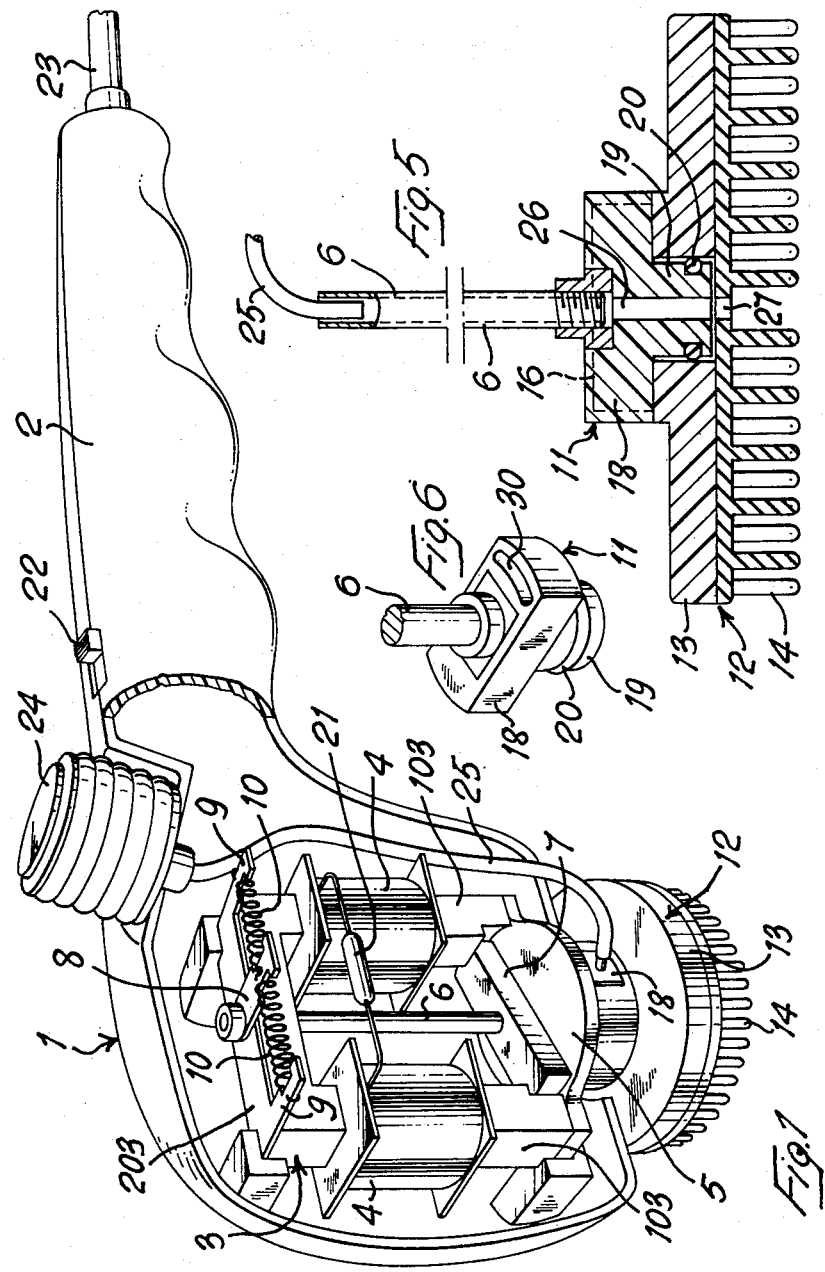

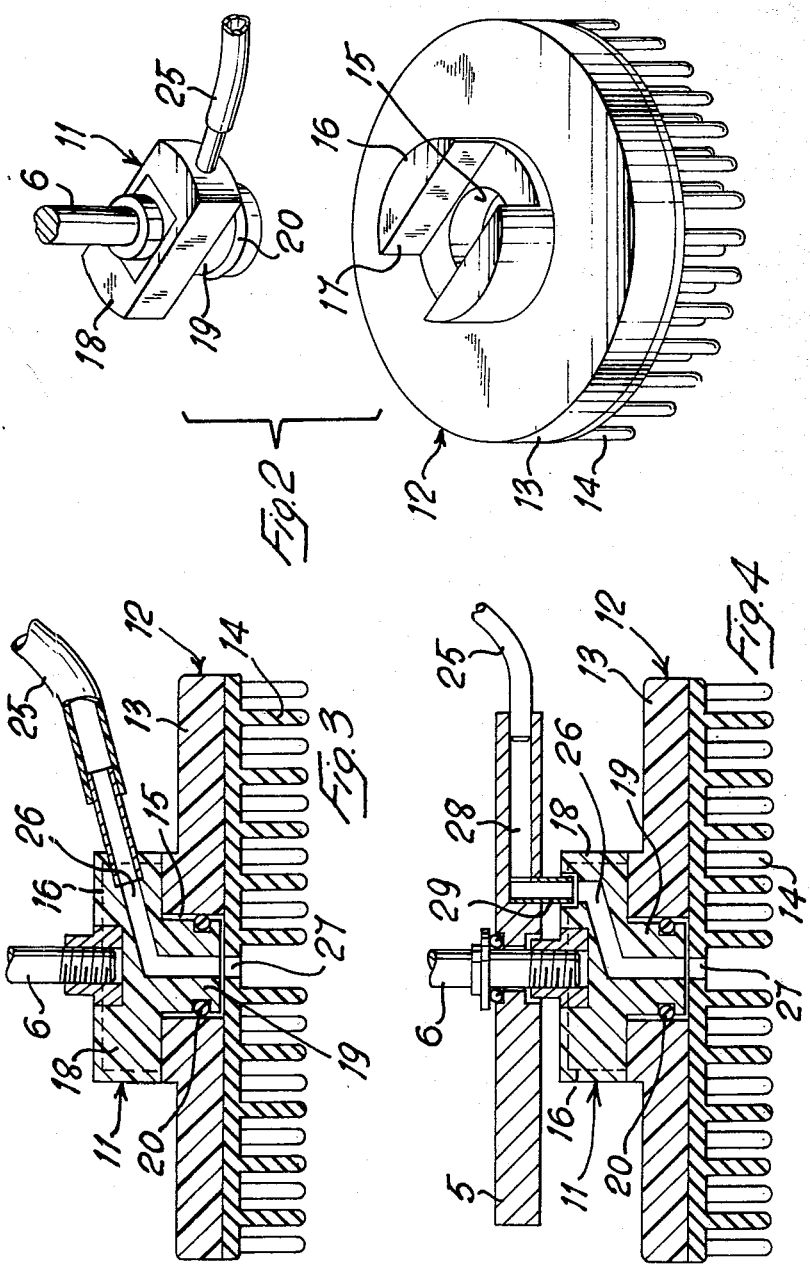

APPARATUS FOR MASSAGING THE SKIN

SUMMARY OF THE INVENTION

The present invention relates to apparatus for massaging the skin, and more particularly for massaging the scalp, and distributing at the same time on the area of the skin undergoing the treatment controlled amounts of lotions or other suitable liquid or pasty substances for cosmetic or curative treatment of the skin.

Substantially, the apparatus comprises a casing provided with a handle, in which casing there is housed a small electric motor capable of imparting to its shaft a movement consisting of rotary oscillations. The shaft carries a skin massaging element, preferably a circular brush, which by being applied onto the skin portion to be subjected to treatment, effects a massage which is characterized by the rotary oscillations of the brush, instead of the vibratory movement of some known massaging apparatuses, or the unidirectional continuous rotary movement of some other known apparatuses.

Another important feature of the apparatus according to the invention consists in the fact that on the same apparatus there is provided a small container for the liquid (lotion) to be dispensed, and a canalization leading from this container directly to the zone undergoing the treatment, and preferably to a dispensing bore obtained in the massaging brush. Suitable means are provided in order to permit the dispensing of controlled amounts of liquid whenever desired.

These and other features of the invention will be clearly understood from the following description of some preferred embodiments thereof with reference to the accompanying drawings, and the novel features will be particularly pointed out in the appended claims.

BRIEF DESCRIPTION OF THE DRAWINGS

FIG. 1 is a perspective view, with parts in section, of the massaging apparatus according to the invention;

FIG. 2 is a perspective view showing a detail of the support plate which is part of the apparatus, and of the circular brush used for massaging, particularly pointing out the system for fitting the brush onto the said support plate;

FIG. 3 is a longitudinal section showing the detail of the support plate and of the brush fitted thereonto;

FIG. 4 is a view similar to that of FIG. 3, showing a modified embodiment of the invention;

FIG. 5 is still a further view similar to that of FIG. 3, showing another modified embodiment of the invention, and FIG. 6 is a perspective view showing the detail of the support plate according to the embodiment shown in FIG. 4.

DESCRIPTION AND OPERATION OF THE PREFERRED EMBODIMENTS

With reference to FIG. 1 of the drawings, the massaging apparatus 1 consists of a casing provided with a suitable handle 2, this casing being preferably made of plastics, and resulting from the assembly of two identical halves or shells. The two shells are provided, in a known manner, with inwardly directed projecting parts, for supporting and securing in place, when they are assembled together, the motor unit consisting of a U-shaped electromagnet 3 having two pole pieces 103 connected at their upper end by a yoke 203. The electromagnet 3 can be made in any suitable manner, but preferably is constructed of sintered material. Onto each one of the two pole pieces 103 there is fitted an electric coil 4, while onto the lower free ends of the said pole pieces 103 there is secured a crosspiece 5, made of non-magnetic material. Through a bore provided in the center of the support plate 5 there passes, in a rotatable manner, a small shaft 6, rotatably supported, at its upper end, by a through bore provided in the yoke 203 of electromagnet 3. The shaft 6 carries in its lower portion, above the support plate 5 and in correspondence of the inner extremities of the pole pieces 103, a rotor 7, which preferably consists of a small bar of ferromagnetic material designed to close the magnetic circuit at the free polar extremities of the U-shaped electromagnet 3. As it can be clearly seen from FIG. 1, the ends of the rotor plate 7 are suitably rounded in order to be movable with the minimum air gap inside cooperatively shaped recesses provided at the inner side of the free polar extremities.

The motor shaft 6 passes through the bore provided in the yoke 203 and carries, keyed at its end projecting over the yoke 203, a small lever arm 8, to which there are secured the ends of two return springs 10, anchored, at their other ends, to side extensions 9 of a small plate secured onto the said yoke portion 203. The angular position of the lever arm 8 with respect to rotor 7 carried by the same shaft 6 is such that normally the same is maintained under the action of return springs 10 at some angle with respect to the ideal line of flow between the polar extremities of the pole pieces 103, said angle being between 5° and 15° and preferably between 8° and 12°.

The motor shaft 6 passes through a bore provided in the crosspiece 5 and terminates (FIGS. 2 to 6) into a brush-carrying member 11, projecting out of a circular opening provided in the bottom portion of the casing of the apparatus. The brush-carrying member 11 consists of a support plate 18, substantially rectangular and provided with a downwardly directed cylindrical appendix or plug 19, having a peripheral groove in which there is arranged an annular friction ring 20. The brush-carrying member is designed to fit inside a complementarily shaped portion provided on the upper surface of a circular brush 12. This complementarily shaped portion consists of a bore or socket 15, provided at the center of the brush and of two projecting parts 16, provided with flanks 17 apt to cooperate with the sides of the rectangular support plate 18.

The circular brush 12 is fitted onto the brush-carrying member by insertion of appendix or plug 19 into the bore 15 of the brush, and it is retained thereonto by the friction cooperation of the elastic ring 20 onto the inner side of said bore 15, thus realizing a removable quick fit connection. The brush 12 consists of a circular bristle-carrying member 13, which is provided on its lower side with bristles 14, which can be of any suitable type, and, in the example as shown, are rather large and thick, sufficiently spaced apart and with rounded tips, preferably made of rubber or rubber-elastic material.

Turning now again to the electric circuit, same is completed by a rectifier diode 21 connecting in series the two coils 4 and by a suitable switch 22 provided on the back of the handle 2, which controls the operation of the motor unit to which alternating current is fed through lead 23.

The operation of the just described apparatus is simple and evident:

By feeding alternating current, the coils, connected in series by diode 21, are passed cyclically in a single direction by a pulsating electric current, with consequent formations, in the magnetic circuit, of an unidirectional magnetic flow which tends to close itself through rotor 7, thus bringing the same cyclically in aligned position with respect to the extremities of pole pieces 3. It derives therefrom that, by virtue of the mentioned pulsating current and of the return springs 10, rotor 7 and shaft 6 are caused to oscillate about the common axis, with a frequency which corresponds to the frequency of the alternating current fed to the coils 4. Thus, with the same frequency, and with an angle of oscillation corresponding to the angle by which the rotor 7 is offset with respect to the pole pieces 103, the circular brush 12 is driven into rotary oscillations which produce the desired massage.

As already mentioned, one of the characteristic features of the apparatus is that of permitting the sprinkling of suitable lotions, creams or liquids onto the parts of the body (scalp or other parts) which undergo the massage treatment. As illustrated in FIG. 1, in the apparatus 1, at a suitable position in proximity of the handle 2 and of the switch 22, there is provided a bellows-shaped removable container 24 for the lotion or other suitable liquid or creamy substance to be dispensed and spread over the skin, in such a position that pressure may be applied onto same (and thus the liquid be discharged, in the manner which will be seen hereafter) by using one of the fingers of the same hand which holds the apparatus. A small flexible pipe 25 is provided which connects the bottom of said container with a duct or canalization 26 (see FIG. 3) provided in the brush carrying member 11 and opening in correspondence of the bottom of the projecting part 19. Correspondingly, in the center portion of the brush a through bore 27 is provided, so that, by applying pressure onto the bellows container 24, a measured amount of liquid is conveyed, through flexible pipe 25, to the brush-carrying member 11, to be finally discharged and spread in correspondence of the center zone of the brush, the whole while the brush is operating, i.e. massaging with rotary oscillations.

In the embodiment shown in FIGS. 4 and 6 there is shown another type of connection between the pipe 25 conveying liquid from the container 24, and the central bore 27 in the brush, where the liquid is finally dispensed. In this embodiment, the pipe is connected to a duct 28 provided in the crosspiece 5, which duct 28 opens, through a small projecting pipe 29, into an arcuate collector slot 30 provided in the brush-carrying member 11 (see particularly FIG. 6). Collector slot 30 is connected through duct 26 to the through bore 27 in the brush. It appears evident that by this arrangement the pipe 25 is not subjected to oscillation movements, and therefore needs not be flexible.

In FIG. 5 there is shown a further embodiment in which pipe 25 leads into a duct provided along the motor shaft 6, which is therefore a hollow shaft. The duct provided in the shaft 6 leads to the canalization 26 in the brush-carrying member and finally to the bore 27 in brush 12.

It will be appreciated that the ring 20, while providing the necessary friction in order to maintain the brush 12 secured in a removable manner to the brush-carrying member 11, will act as sealing ring in order to avoid leaks of the liquid being dispensed upstream of dispensing bore 27.

It will be also appreciated that the apparatus may be subjected to various variations and modifications, particularly in its connection details, without departing from the inventive ideas as above expressed and claimed hereafter. Thus, it will be evident that for the apparatus any other suitable motor may be provided which will drive the shaft 6 into rotary oscillations.

It is believed that the invention will have been clearly understood from the foregoing detailed description of the preferred embodiments. Changes in the details of construction may be resorted to without departing from the spirit of the invention, and it is accordingly intended that no limitation be implied and that the hereto annexed claims be given the broadest interpretation to which the employed language fairly admits.

I claim:
1. Apparatus for massaging the skin, comprising:
   a. a casing provided with a handle;
   b. an electric motor having a shaft, housed in said casing and being capable of imparting to said shaft a rotary oscillatory movement;
   c. support means for carrying a skin massaging element, comprising a non circular support plate, integral with said shaft for rotation therewith, said plate being provided with a circular plug, coaxial with said motor shaft;
   d. a skin massaging element, comprising a brush having a dispensing bore for fluid formed therein, provided with a non circular recess and with a cylindrical socket, said recess and said socket being adapted to complementarily removably receive respectively said support plate and said plug;
   e. a container for a liquid or pasty substance, arranged on the casing in proximity to said handle and being provided with at least a flexible portion adapted to be manually pressed; and
   f. conduit means for connecting said container to said dispensing bore in said brush,
      whereby said liquid may be dispensed during rotation of said brush.

2. The apparatus for massaging the skin according to claim 1 including means for casing a controlled outflow of the liquid or pasty substance from the container to said dispensing bore.

3. The apparatus for massaging the skin according to claim 1, in which the angle of the rotary oscillation imparted by the electric motor to its shaft is comprised between 5° to 15°.

4. The apparatus for massaging the skin according to claim 1, in which the conduit means comprises a flexible pipe leading from the container to a duct formed in the support plate and opening in correspondence to said dispensing bore in the brush.

5. The apparatus for massaging the skin according to claim 1, in which the conduit means comprises a pipe leading from the container to a duct coaxially formed in the motor shaft, said duct being connected to a second duct formed in the support plate and opening in correspondence to the dispensing bore in the brush.

6. The apparatus for massaging the skin according to claim 1, in which the conduit means comprises a small pipe leading to a duct formed in a fixed cross-piece member provided above the movable support plate, said duct opening in correspondence to a collector slot formed in the movable support plate, said collector slot leading, through a duct formed in said movable support plate, to the dispensing bore in the brush.

* * * * *